US007011941B1

(12) United States Patent
Akerblom

(10) Patent No.: US 7,011,941 B1
(45) Date of Patent: Mar. 14, 2006

(54) HUMAN EOSINOPHIL-DERIVED BASIC PROTEIN

(75) Inventor: Ingrid E. Akerblom, Redwood City, CA (US)

(73) Assignee: Incyte Corporation, Wilmington, DE (US)

( * ) Notice: Subject to any disclaimer, the term of this patent is extended or adjusted under 35 U.S.C. 154(b) by 878 days.

(21) Appl. No.: 09/645,399

(22) Filed: Aug. 24, 2000

Related U.S. Application Data

(62) Division of application No. 09/040,483, filed on Mar. 17, 1998, now Pat. No. 6,143,867, which is a division of application No. 08/740,036, filed on Oct. 23, 1996, now Pat. No. 5,728,820.

(51) Int. Cl.
*C12Q 1/68* (2006.01)
*C07H 21/02* (2006.01)
*C07H 21/04* (2006.01)

(52) U.S. Cl. .......................................... 435/6; 536/23.5
(58) Field of Classification Search .................... 435/6, 435/29, 325; 536/23.5
See application file for complete search history.

(56) References Cited

FOREIGN PATENT DOCUMENTS

WO      WO 97/37022      10/1997

OTHER PUBLICATIONS

Skolnick et al Trends in Biotech 18(1):34-39, 2000.*
Sequence Alignment of Accession AA779195 to SEO ID No.: 2.*
Whisstock, JC et al. Quarterly Rev. Immunol. [2003] 36(3): 307-340.*
Gleich et al., "The eosinophil as a mediator of damage to respiratory epithelium: A model for bronchial hyperreactivity," *J. Allergy Clin. Immun.*, 81 (5) (1) :776-781.
Frigas et al., "Elevated Levels of the Eosinophil Granule Major Basic Protein in the Sputum of Patients with Bronchial Asthma," *Mayo Clin. Proc.*, 56:345-353.
Filley et al., "Identification By Immunofluorescence of Eosinophil, Granule, Major Basic Protein in Lung Tissues of Patients with Bronchial Asthma", *Lancet*, 2:11-16 (Jul. 3, 1982).
Sarmiento et al., "IL-3, IL-5, and Granulocyte-Macrophage Colony-Stimulating Factor Potentiate Basophil Mediator Release Stimulated by Eosinophil Granule Major Basic Protein," *J. Immunol.*, 155:2211-2221.
Moy et al., Identification of an IgA inhibitor of neutrophil chemotaxis and its membrane target for the metabolic burst, *J. Immunol.*, 145:2626-2632.
Rohrbach et al., "Activation of Platelets by Eosinophil Granule Proteins" *J. Exp. Med.*, 145:1271-1274 (1990).

Kita et al., "Eosinophil Major Basic Protein Induces Degranulation and IL-8 Production by Human Eosinophils1," *The Journal of Immunology*, 154:4749-4758 (1995).
Popken-Harris et al., "Expression, Purification, and Characterization of the Recombinant Proform of Eosinophil Granule Major Basci Protein," *J. Immunol.*, 155:1472-1480 (1995).
Oxvig, et al., "Localization of disulfide bridges and free sulfyhdryl groups in human eosinophil granule major basic protein," *FEBS Lett.*, 341:213-217 (1994).
Abu-Ghazaleh, "Interaction of Eosinophil Granule Major Basic Protein with Synthetic Lipid Bilayers: A Mechanism for Toxicity," *J. Membrane Biol.*, 128:153-164 (1992).
Wagner, "Pregnancy-Associated Major Basic Protein: Deposition of Protein and Expression of mRNA at the Maternal-Fetal Junction in Early and Late Gestation," *Placenta*, 15:625-640 (1994).
Maddox, "Localization of a Molecule Immunochemically Similar to Eosinophil Major Basic Protein in Human Placenta," *J. Exp. Med.*, 160:29-41 (1984).
Oxvig, "Circulating Human Pregnancy-Associated Plasma Protein-A Is Disulfide-bridged to the Proform of Eosinophil Major Basic Protein," *The Journal of Biological Chemistry*, 268(17):12243-12246 (1993).
Oxvig, "Identification of Angiotensinogen and Complement C3dg ans Novel Proteins Binding the Proform of Eosinophil Major Basic Protein in Human Pregnancy Serum and Plasma," *The Journal of Biological Chemistry*, 270(23): 13645-13651 (1995).
Brambati et al., "Low Material Serum levels of pregnancy associated plasma protein A (PAPP-A) in the first trimester in association with abnormal fetal karyotype," *British Journal of Obstetrics and Gynecology*, 100:324-326 (Apr. 1993).

(Continued)

*Primary Examiner*—Christina Chan
*Assistant Examiner*—F. Pierre VanderVegt
(74) *Attorney, Agent, or Firm*—Foley & Lardner LLP

(57) ABSTRACT

The present invention provides a human eosinophil-derived basic protein (EBPH) and polynucleotides which identify and encode EBPH. The invention also provides genetically engineered expression vectors and host cells comprising the nucleic acid sequences encoding EBPH and a method for producing EBPH. The invention also provides for use of EBPH and agonists, antibodies or antagonists specifically binding EBPH, in the prevention and treatment of diseases associated with expression of EBPH. Additionally, the invention provides for the use of antisense molecules to polynucleotides encoding EBPH for the treatment of diseases associated with the expression of EBPH. The invention also provides diagnostic assays which utilize the polynucleotide, or fragments or the complement thereof, and antibodies specifically binding EBPH.

4 Claims, 6 Drawing Sheets

OTHER PUBLICATIONS

Tewksbury et al., "Immunochemical Comparison of High Molecular Weight Angiotensinogen from Amniotic Fluid, Plasma of Men, and Plasma of Pregnant Women," *J. Exp. Med.*, 168:1493-1498 (1988).

Barker et al., "Acidic Precursor Revealed in Human Eosinophil Granule Major Basic Protein cDNA," *J. Exp. Med.*, 168:1493-1498 (Sep. 1988).

Aoki et al., "Comparison of the amino acid and nucleotide sequences between human and two guinea pig major basic proteins," *FEBS Letters*, 282(1): 56-60.

Barker, R.L. et al., "Cloning and sequence analysis of the human gene encoding eosinophil major basic protein", *Gene*, 86:285-289 (1990).

Mikayama, T. et al., "Molecular cloning and functional expression of a cDNA encoding glycosylation-inhibiting factor", *Proc. Natl. Acad. Sci. USA*, 90:10056-10060 (1993).

Voet, D. and Voet, JG. In: Biochemistry. Voet and Voet, eds. John Wiley & Sons, Inc. New York, pp. 126-128 and 2228-2234 (1990).

GeneSeq entry W31527; May 21, 1998; Gentz R.L. et al. (1998).

Alignment Report; Apr. 10, 2000 (2000).

* cited by examiner

```
5' GACGG CTC GAG TGG AGG TCT CAG ACT CTT GGA AGG GGC TAT ACT AGA CAC ACA AAG
                11      20          29          38          47          56

ACA GCC CCA AGA AGG ACG GTG GAG TGT CCT TAG TGT CGC TAA AAG ACA GTA GAT ATG
        65          74          83          92         101         110   M

CAA CGC CTC TTG CTC CTG CCC TTT CTC CTG CTG GGA ACA GTT TCT GCT CTT CAT
 Q   R   L   L   L   L   P   F   L   L   L   G   T   V   S   A   L   H
       119         128         137         146         155         164

CTG GAG AAT GAT GCC CCC CAT CTG GAG AGC CTA GAG ACA CAG GCA GAC CTA GGC
 L   E   N   D   A   P   H   L   E   S   L   E   T   Q   A   D   L   G
       173         182         191         200         209         218

CAG GAT CTG GAT AGT TCA AAG GAG CAG GAG AGA GAC TTG GCT CTG ACG GAG GAG
 Q   D   L   D   S   S   K   E   Q   E   R   D   L   A   L   T   E   E
       227         236         245         254         263         272

GTG ATT CAG GCA GAG GGA GAG GAG GTC AAG GCT TCT GCC TGT CAA GAC AAC TTT
 V   I   Q   A   E   G   E   E   V   K   A   S   A   C   Q   D   N   F
       281         290         299         308         317         326

GAG GAT GAG GAA GCC ATG GAG TCG CCA GCT GCC TTA GAC AAG GAC TTC CAG
 E   D   E   E   A   M   E   S   P   A   A   L   D   K   D   F   Q
       335         344         353         362         371         380
```

FIGURE 1A

```
     389           398           407           416           425           434
TGC  CCC  AGG  GAA  GAA  GAC  ATT  GTT  GAA  GTG  CAG  GGA  AGT  CCA  AGG  TGC  AAG  ACC
 C    P    R    E    E    D    I    V    E    V    Q    G    S    P    R    C    K    T 443           452           461           470           479           488
TGC  CGC  TAC  CTA  TTG  GTG  CGG  ACT  CCT  AAA  ACT  TTT  GCA  GAA  GCT  CAG  AAT  GTC
 C    R    Y    L    L    V    R    T    P    K    T    F    A    E    A    Q    N    V 497           506           515           524           533           542
TGC  AGC  AGA  TGC  TAC  GGA  GGC  AAC  CTT  GTC  TCT  ATC  CAT  GAC  TTC  AAC  TTC  AAC
 C    S    R    C    Y    G    G    N    L    V    S    I    H    D    F    N    F    N 551           560           569           578           587           596
TAT  CGC  ATT  CAG  TGC  ACT  AGC  ACA  GTC  AAC  GCC  CAG  GTC  TGG  ATT  GGA
 Y    R    I    Q    C    T    S    T    V    N    A    Q    V    W    I    G 605           614           623           632           641           650
GGC  AAC  CTC  AGG  GGC  TGG  TTC  CTG  TGG  AAG  CGG  TTT  TGC  TGG  ACT  GAT  GGG  AGC
 G    N    L    R    G    W    F    L    W    K    R    F    C    W    T    D    G    S 659           668           677           686           695           704
CAC  TGG  AAT  TTT  GCT  TAC  TGG  TCC  CCA  GGG  CAA  CCT  GGG  AAT  GGG  CAA  GGC  TCC
 H    W    N    F    A    Y    W    S    P    G    Q    P    G    N    G    Q    G    S 713           722           731           740           749           758
TGT  GTG  GCC  CTA  TGC  ACC  AAA  GGA  GGT  TAT  TGG  CGA  CGA  GCT  CAA  TGC  GAC  AAG
 C    V    A    L    C    T    K    G    G    Y    W    R    R    A    Q    C    D    K
```

FIGURE 1B

```
       767     776     785     794     803     812
CAA CTG CCC TTC GTC TGC TCC TTC TAA GCC AGC GGC ACG GAG ACC CTG CCA GCA
 Q   L   P   F   V   C   S   F 821     830     839     848     857
GCT CCC TCC CGT CCC CCA ACC TCT CCT GCT CAT AAA TCC AGA CTT CCC ACA GC 3'
```

FIGURE 1C

```
  1 MQRLLLPFLLLGTVSALHLENDAPHLESLETQADLGQDL   EBPH
  1 MKLPLLLA-LLEGAVSALHLRSETSTFETPLGAKTLPEDE  GI 34476
  1 MKLLLLLA-LLLGAVSTRHLKVDTSSLQSLRGEESLAQDG  GI 220291
  1 MKLLLLLA-LLVGAVSTRHLNVDTSSLQGEESLAQDG     GI 544241

41 DSSKEQERD-----LALTEEVIQA-EGEEVKASACQDNF   EBPH
 40 ETPEQEMEETPC------RLEEEEWGSGSEDASKKDG     GI 34476
 40 ETAEGATREATAGALMPLPEE--EEMEGASGSEDDPEEEE  GI 220291
 40 ETAEGATREAASGVLMPLREEVKEEMEGGSGSEDDPEEEE  GI 544241

74 EDEEAME---SDPAALDKDFQCPREEDIVEVQGSPRCKTCR EBPH
 73 A----VESISVPDMVDKNLTCPEEEDTVKVVGIPGCQTCR  GI 34476
 78 EEEVEFSSELDVSPEDIQCPKEEDTVKFFSRPGYKTRG    GI 220291
 80 EEKE-IMESSELDMGPEDVQCPKEEDIVKFEGSPGCKICR  GI 544241

112 YLLVRTPKTFAEAQNVCSRCYGGNLVSIHDFNFNYRIQCC  EBPH
109 YLLVRISLQTFSQAWFTCRRCYRGNLVSIHNFNINYRIQCS GI 34476
118 YVMVGSARTFNEAQWVCQRCYRGNLASIHSEAFNYQVQCT  GI 220291
119 YVVLSVPKTFKQAQSVCQRCFRGNLASIHSYNINLQVQRS  GI 544241
```

HUMAN EOSINOPHIL-DERIVED BASIC PROTEIN

This application is a divisional application of U.S. application Ser. No. 09/040,483, filed Mar. 17, 1998, U.S. Pat. No. 6,143,867 which is a divisional application of U.S. application Ser. No. 08/740,036, filed on Oct. 23, 1996, now U.S. Pat. No. 5,728,820, issued Mar. 17, 1998, both entitled NOVEL HUMAN EOSINOPHIL-DERIVED BASIC PROTEIN, all of which applications and patents are hereby incorporated herein by reference.

FIELD OF THE INVENTION

This invention relates to nucleic acid and amino acid sequences of a novel human eosinophil-derived basic protein and to the use of these sequences in the diagnosis, prevention, and treatment of disease.

BACKGROUND OF THE INVENTION

Stem cells are progenitor blood cells which differentiate to mature white blood cells, red blood cells, and platelets. Stem cells are found in adult bone marrow, in fetal liver and spleen, and in blood collected from the umbilical cord after the birth of a baby.

Eosinophil growth and differentiation from stem cells is regulated by hematopoietic growth factors including granulocyte-macrophage colony stimulating factor (GM-CSF), interleukin-3 (IL-3), and interleukin-5 (IL-5). IL-5 is a potent eosinophil differentiation and activation factor, while GM-CSF and IL-3 also increase the production of other myeloid cells.

Eosinophils are white blood cells which are sub-classified as granulocytes due to the presence of large, coarse membrane-bound cytoplasmic granules. These granules contain proteins and other compounds which carry out a variety of inflammatory and immune functions. In response to chemotactic factors, eosinophils migrate through blood vessel walls and through tissues to the site where they are needed. There the contents of the granules are released in response to specific stimuli. Eosinophil granule release is stimulated by immunoglobulin E (IgE)-mediated hypersensitivity reactions such as parasitic infections and type I allergic reactions. Such type I allergic reactions include asthma and allergic rhinitis.

A variety of eosinophil-derived basic proteins (EDBPs) are released from eosinophil granules. These cytotoxic proteins disrupt membrane surfaces and lyse cells. EDBPs are thus potent anti-parasitic and anti-bacterial agents, however, EDBPs may also damage host tissues. For instance, the cardiovascular damage associated with chronic hypereosinophilia has been attributed in part to secreted EDBPs. EDBPs have been shown to damage respiratory epithelial cells, and have been implicated in the increase in bronchial hyperreactivity frequently observed in asthma patients. A significant correlation exists between the intensity of bronchial hyperreactivity and the levels of EDBPs in blood and bronchoalveolar lavage (BAL) fluid from asthmatics.

Eosinophil granule major basic protein (MBP), one of the most extensively characterized EDBPs, is a potent toxin against helminths, protozoa, bacteria and other cells. MBP also causes epithelial desquamization and ciliostasis, effects that mimic the pathology of asthma (Gleich, G. J. et al. (1988) J. Allergy Clin. Immun. 81:776–781). MBP is found in sputa and on damaged bronchial tissues of asthma patients (Frigas, E. et al. (1981) Mayo Clin. Proc. 56:345; Filley, W. V. et al. (1982) Lancet 2:11).

Along with its cytolytic properties, MBP also possesses noncytolytic proinflammatory properties, many of which are associated with late phase reactions of allergic disease. The release of histamine and leukotriene C4 from basophils is stimulated by MBP and further enhanced by the cytokines IL-3, IL-5 and GM-CSF (Sarmiento, E. U. et al. (1995) J. Immunol. 155:2211–2221). MBP also stimulates neutrophil activation and degranulation, including the release of superoxide anion (O2—) and lysozyme (Moy, J. N. et al. (1990) J. Immunol. 145:2626–2632), and platelet activation (Rohrbach, M. S. et al. (1990) J. Exp. Med. 172:1271–1274). MBP also induces further eosinophil degranulation (Kita, H. et al. (1995) J. Immunol. 154:4749–4758).

The cDNA for MBP encodes a 25 kdal preproprotein molecule of 222 amino acids, which includes a predicted 15 amino acid leader peptide, a 90 amino acid acidic pro domain and a 117 amino acid mature polypeptide (Popken-Harris, P. et al. (1995) J. Immunol. 155:1472–1480). The pro domain of MBP contains a heterogeneous population of O— and N-linked glycosyl modifications and has an isoelectric point (pI) of approximately 4.9. The 14 kdal mature MBP contains two disulfide bridges and five free cysteine residues (Oxvig, C. et al. (1994) FEBS Lett. 341:213–217).

The negatively-charged pro domain appears to interact with the positively-charged mature MBP. This interaction is proposed to inhibit the activity of mature MBP thus protecting the developing eosinophil from damage by MBP during granule processing (Popken-Harris, et al. (1995), supra). Mature MBP, but not proMBP, reacts readily with acidic lipids and disorders lipid bilayers resulting in the lysis of liposomes (Abu-Ghazaleh, R. I. et al. (1992) J. Membr. Biol. 128:153–164). Unlike mature MBP, proMBP does not stimulate basophil histamine release or neutrophil superoxide generation; in fact, proMBP is an inhibitor of these MPB-stimulated activities (Popken-Harris, et al. (1995), supra).

ProMBP is expressed in placental X cells and is found in the sera of pregnant women (Wagner, J. M. et al. (1994) Placenta 15:625–640). Levels of proMBP peak before labor and rapidly decline after delivery (Maddox, D. E. et al. (1983) J. Exp. Med. 158:1211–1216). ProMBP of placental origin is heavily glycosylated and circulates in disulfide-bridged complexes with pregnancy-associated plasma protein A (PAPP-A), angiotensinogen, and complement C3dg (Oxvig C. et al. (1993) J. Biol. Chem. 268:12243–12246; Oxvig C. et al (1995) J. Biol. Chem. 270:13645–13651). Low serum levels of PAPP-A in the first trimester have been linked to fetal chromosomal abnormalities (Brambati, M. C. (1993) Br. J. Obstet. Gynaecol. 100:324–326). A high molecular weight (HMW) form of angiotensinogen has been found in moderate quantities in plasma from pregnant women and in high quantities in hypertensive pregnant women (Tewksbury, D. A. et al. (1989) Am. J. Hypertens. 2:411–413). Oxvig and colleagues (1995, supra) suggest that this HMW angiotensinogen is actually the proMBP:angiotensinogen complex.

The discovery of polynucleotides encoding a novel EDBP-like molecule, and the molecule themselves, satisfies a need in the art by providing a new means for the diagnosis, prevention, or treatment of diseases and conditions associated with eosinophil accumulation and granule release including late-phase allergic/inflammatory reactions, eosinophilias, parasitic infections, and conditions associated with placental derived-EDBP accumulation in pregnancy.

SUMMARY OF THE INVENTION

The present invention features a novel basic protein derived from IL-5 cultured umbilical cord blood cells, hereinafter designated as EBPH and characterized as having chemical and structural homology to eosinophil granule MBPs from human and guinea pig.

Accordingly, the invention features a substantially purified human EBPH having the structural characteristics of the MBPs above and as shown in amino acid sequence, SEQ ID NO:1.

One aspect of the invention features isolated and substantially purified polynucleotides that encode EBPH. In a particular aspect, the polynucleotide is the nucleotide sequence of SEQ ID NO:2.

The invention also features a polynucleotide sequence comprising the complement of SEQ ID NO:2 or variants thereof. In addition, the invention features polynucleotide sequences which hybridize under stringent conditions to SEQ ID NO:2.

The invention additionally features nucleic acid sequences encoding polypeptides, oligonucleotides, peptide nucleic acids (PNA), fragments, portions or antisense molecules thereof, and expression vectors and host cells comprising polynucleotides that encode EBPH. The present invention also features antibodies which bind specifically to EBPH, and pharmaceutical compositions comprising substantially purified EBPH. The invention also features agonists and antagonists of EBPH.

BRIEF DESCRIPTION OF THE FIGURES

FIGS. 1A, 1B, and 1C show the amino acid sequence (SEQ ID NO:1) and nucleic acid sequence (SEQ ID NO:2) of EBPH. The alignment was produced using MacDNASIS PRO™ software (Hitachi Software Engineering Co., Ltd., San Bruno, Calif.).

Figure 2B:
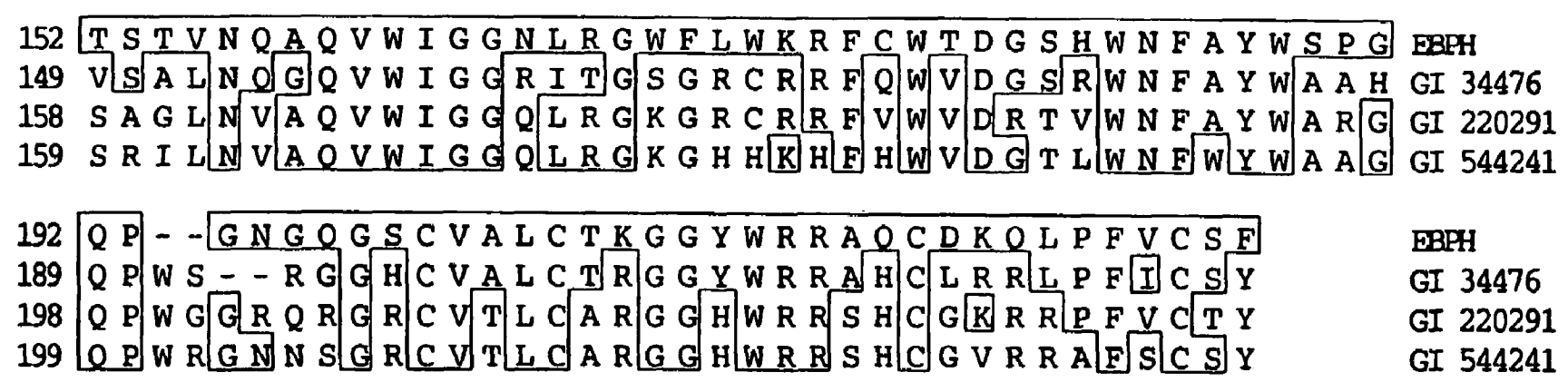

FIGS. 2A and 2B shows the amino acid sequence alignments among EBPH (SEQ ID NO:1), eosinophil granule MBP from human (GI 34476; SEQ ID NO:3) and two MBP homologs from guinea pig, GMBP-1 (GI 220291; SEQ ID NO:4), and GMBP-2 (GI 544241, SEQ ID NO:5). The alignment was produced using the multisequence alignment program of DNASTAR™ software (DNASTAR Inc, Madison Wis.).

DESCRIPTION OF THE INVENTION

Figure 3:
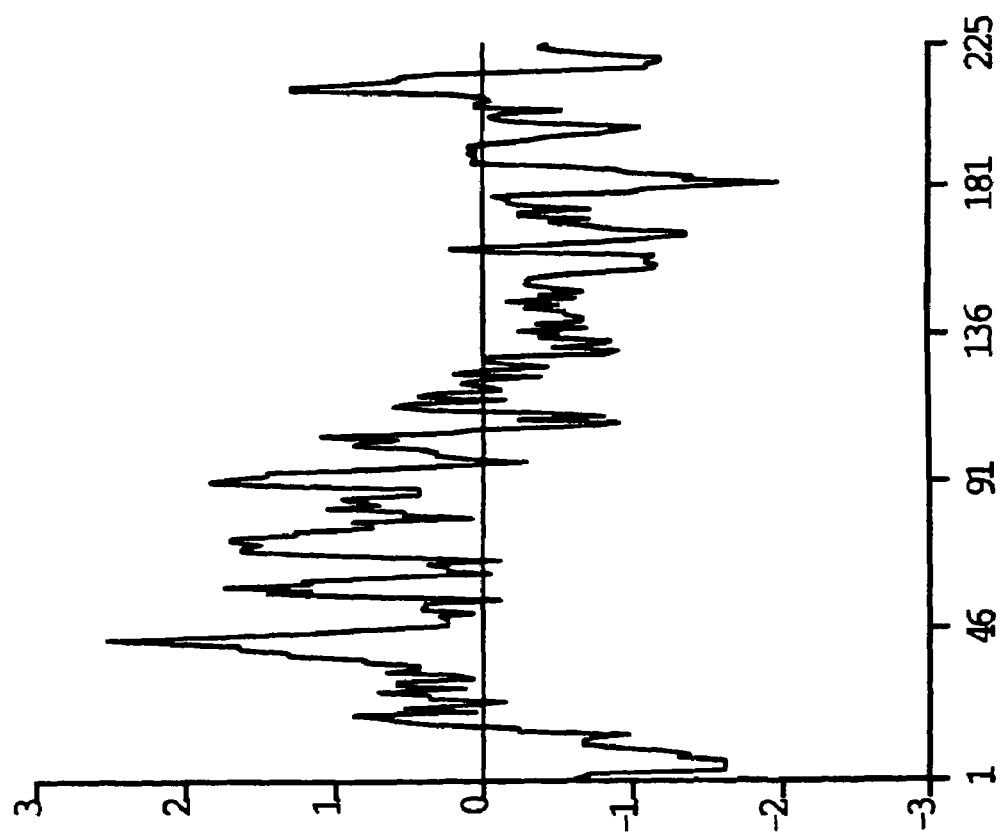
FIG. 3 shows the hydrophobicity plot (MacDNASIS PRO software) for EBPH, SEQ ID NO:1; the positive X axis reflects amino acid position, and the negative Y axis, hydrophobicity.

Before the present protein, nucleotide sequence, and methods are described, it is understood that this invention is not limited to the particular methodology, protocols, cell lines, vectors, and reagents described as these may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

Definitions

"Nucleic acid sequence" as used herein refers to an oligonucleotide, nucleotide, or polynucleotide, and fragments or portions thereof, and to DNA or RNA of genomic or synthetic origin which may be single- or double-stranded, and represent the sense or antisense strand. Similarly, "amino acid sequence" as used herein refers to an oligopeptide, peptide, polypeptide, or protein sequence and fragments or portions thereof, of a naturally occurring or synthetic molecule.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

"Peptide nucleic acid", as used herein, refers to a molecule which comprises an oligomer to which an amino acid residue, such as lysine, and an amino group have been added. These small molecules, also designated anti-gene agents, stop transcript elongation by binding to their complementary strand of nucleic acid (Nielsen, P. E. et al. (1993) Anticancer Drug Des. 8:53–63).

EBPH, as used herein, refers to the amino acid sequences of substantially purified EBPH obtained from any species, particularly mammalian, including bovine, ovine, porcine, murine, equine, and preferably human, from any source whether natural, synthetic, semi-synthetic, or recombinant.

"Consensus", as used herein, refers to a nucleic acid sequence which has been resequenced to resolve uncalled bases, or which has been extended using XL-PCR™ (Perkin Elmer, Norwalk, Conn.) in the 5' and/or the 3' direction and resequenced, or which has been assembled from the overlapping sequences of more than one Incyte clone using the GCG Fragment Assembly™ system (GCG, Madison, Wis.), or which has been both extended and assembled.

A "variant" of EBPH, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

A "deletion", as used herein, refers to a change in either amino acid or nucleotide sequence in which one or more amino acid or nucleotide residues, respectively, are absent.

An "insertion" or "addition", as used herein, refers to a change in an amino acid or nucleotide sequence resulting in the addition of one or more amino acid or nucleotide residues, respectively, as compared to the naturally occurring molecule.

A "substitution", as used herein, refers to the replacement of one or more amino acids or nucleotides by different amino acids or nucleotides, respectively.

The term "biologically active", as used herein, refers to a protein having structural, regulatory, or biochemical functions of a naturally occurring molecule. Likewise, "immunologically active" refers to the capability of the natural, recombinant, or synthetic EBPH, or any oligopeptide thereof, to induce a specific immune response in appropriate animals or cells and to bind with specific antibodies.

The term "agonist", as used herein, refers to a molecule which, when bound to EBPH, causes a change in EBPH which modulates the activity of EBPH. Agonists may include proteins, nucleic acids, carbohydrates, or any other molecules which bind to EBPH.

The terms "antagonist" or "inhibitor", as used herein, refer to a molecule which, when bound to EBPH, blocks the activity of EBPH. Antagonists and inhibitors may include proteins, nucleic acids, carbohydrates, or any other molecules which bind to EBPH.

The term "modulate", as used herein, refers to a change or an alteration in the biological activity of EBPH. Modulation may be an increase or a decrease in protein activity, a change in binding characteristics, or any other change in the biological, functional or immunological properties of EBPH.

The term "mimetic", as used herein, refers to a molecule, the structure of which is developed from knowledge of the structure of EBPH or portions thereof and, as such, is able to effect some or all of the actions of EBPH.

The term "derivative", as used herein, refers to the chemical modification of a nucleic acid encoding EBPH or the encoded EBPH. Illustrative of such modifications would be replacement of hydrogen by an alkyl, acyl, or amino group. A nucleic acid derivative would encode a polypeptide which retains essential biological characteristics of the natural molecule.

The term "substantially purified", as used herein, refers to nucleic or amino acid sequences that are removed from their natural environment, isolated or separated, and are at least 60% free, preferably 75% free, and most preferably 90% free from other components with which they are naturally associated.

"Amplification" as used herein refers to the production of additional copies of a nucleic acid sequence and is generally carried out using polymerase chain reaction (PCR) technologies well known in the art (Dieffenbach, C. W. et al. (1995) *PCR Primer, a Laboratory Manual*, Cold Spring Harbor Press, Plainview, N.Y.).

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., membranes, filters, chips, pins or glass slides to which cells have been fixed for in situ hybridization).

The terms "complementary" or "complementarity", as used herein, refer to the natural binding of polynucleotides under permissive salt and temperature conditions by base-pairing. For example, for the sequence "A-G-T" bonds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between the nucleic acids strands.

The term "homology", as used herein, refers to a degree of complementarity. There may be partial homology or complete homology (i.e., identity). A partially complementary sequence is one that at least partially inhibits an identical sequence from hybridizing to a target nucleic acid; it is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding the probe will not hybridize to the second non-complementary target sequence.

As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

The term "stringent conditions", as used herein, is the "stringency" which occurs within a range from about Tm-5° C. (5° C. below the melting temperature (Tm) of the probe) to about 20° C. to 25° C. below Tm. As will be understood by those of skill in the art, the stringency of hybridization may be altered in order to identify or detect identical or related polynucleotide sequences.

The term "antisense", as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense strand, and "positive" is sometimes used in reference to the sense strand.

The term "portion", as used herein, with regard to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO:1" encompasses the full-length human EBPH and fragments thereof.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but are not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "antigenic determinant", as used herein, refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or "specifically binding". as used herein, in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to proteins in general. For example, if an antibody is specific for epitope "A", the presence of a protein containing epitope A (or free, unlabeled A) in a reaction containing labeled "A" and the antibody will reduce the amount of labeled A bound to the antibody.

The term "sample", as used herein, is used in its broadest sense. A biological sample suspected of containing nucleic acid encoding EBPH or fragments thereof may comprise a cell, chromosomes isolated from a cell (e.g., a spread of metaphase chromosomes), genomic DNA (in solution or bound to a solid support such as for Southern blot analysis), RNA (in solution or bound to a solid support such as for northern blot analysis), cDNA (in solution or bound to a solid support), extract from cells or a tissue, and the like.

The term "correlates with expression of a polynucleotide", as used herein, indicates that the detection of the presence of ribonucleic acid that is complementary to SEQ ID NO:2 by northern analysis hybridization assays is indicative of the presence of mRNA encoding EBPH in a sample and thereby correlates with expression of the transcript from the gene encoding the protein.

"Alterations" in the polynucleotide of SEQ ID NO: 2, as used herein, comprise any alteration in the sequence of polynucleotides encoding EBPH including deletions, insertions, and point mutations that may be detected using hybridization assays. Included within this definition is the detection of alterations to the genomic DNA sequence which encodes EBPH (e.g., by alterations in the pattern of restriction fragment length polymorphisms capable of hybridizing to SEQ ID NO:2), the inability of a selected fragment of SEQ ID NO: 2 to hybridize to a sample of genomic DNA (e.g., using allele-specific oligonucleotide probes), and improper or unexpected hybridization, such as hybridization to a locus other than the normal chromosomal locus for the polynucleotide sequence encoding EBPH (e.g., using fluorescent in situ hybridization (FISH) to metaphase chromosomes spreads).

As used herein, the term "antibody" refers to intact molecules as well as fragments thereof, such as Fa, $F(ab')_2$, and Fv, which are capable of binding the epitopic determinant. Antibodies that bind EBPH polypeptides can be prepared using intact polypeptides or fragments containing small peptides of interest as the immunizing antigen. The polypeptide or peptide used to immunize an animal can be derived from translated cDNA or synthesized chemically, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

The term "humanized antibody", as used herein, refers to antibody molecules in which amino acids have been replaced in the non-antigen binding regions in order to more closely resemble a human antibody, while still retaining the original binding ability.

The Invention

The invention is based on the discovery of eosinophil-derived basic protein (EBPH), the polynucleotides encoding EBPH, and the use of these compositions for the diagnosis, prevention, or treatment of disorders associated with excessive eosinophil accumulation and degranulation such as type I allergic reactions, or disorders in pregnancy related to placental-derived EBPH.

Nucleic acids encoding the human EBPH of the present invention were first identified in cDNA, Incyte Clone 1525913, from an IL-5 stimulated umbilical cord blood cDNA library (UCMCL5T01), through a computer-generated search for amino acid sequence alignments. A consensus sequence, SEQ ID NO:2, was derived from the following overlapping and/or extended nucleic acid sequences: Incyte Clones 1525915, 1488589, 1486890, and 1491748, all from the UCMCL5T01 cDNA library.

In one embodiment, the invention encompasses EBPH, a polypeptide comprising the amino acid sequence of SEQ ID NO:1, as shown in FIGS. 1A, 1B, and 1C. EBPH is 225 amino acids in length. EBPH has chemical and structural homology (FIGS. 2A and 2B) with human MBP (GI 34476; SEQ ID NO:3), guinea pig GMBP-1 (GI 220291; SEQ ID NO:4), and GMBP-2 (GI 544241; SEQ ID NO:5). In particular, EBPH and MBP share 48% identity, EBPH and GMBP-1 share 47% identity, and EBPH and GMBP-2 share 47% identity. As illustrated by FIGS. 2A, 2B, and 3, EBPH is expressed as a preproprotein, with a signal peptide predicted to extend from residues 1 to 16, an acidic pro domain predicted to extend from residues 17 to 108, and the basic mature coding region predicted to extend from residues 109 to 225. The entire 225 amino acid prepro-EBPH protein coding region contains 13 cysteines and no potential N-linked glycosylation sites. The deduced 116 amino acid mature coding region of EBPH contains 10 cysteines. A C-type lectin domain consensus sequence pattern extends from amino acids 200 to 216. The C-type lectin domain structure contains two disulfide bonds. The predicted isoelectric point (pI) for prepro-EBPH is 4.6 and for mature EBPH is 9.6, assuming the formation of two disulfide bonds in the lectin domain.

The sequence identity of MBP, GMBP-1 and GMBP-2 to EBPH decreases in the pro domain coding regions and increases in the mature coding regions. The identity of MBP, GMBP-1 and GMBP-2 to EBPH in the pro-regions is 27%, 33%, and 38%, respectively, while the identity in the mature coding regions is 63%, 56%, and 53%, respectively. The decreased identity in the pro domains may be indicative of different functions for proEBPH and proMBP.

The invention also encompasses EBPH variants. A preferred EBPH variant is one having at least 80%, and more preferably 90%, amino acid sequence similarity to the EBPH amino acid sequence (SEQ ID NO: 1). A most preferred EBPH variant is one having at least 95% amino acid sequence similarity to SEQ ID NO:1.

The invention also encompasses polynucleotides which encode EBPH. Accordingly, any nucleic acid sequence which encodes the amino acid sequence of EBPH can be used to generate recombinant molecules which express EBPH. In a particular embodiment, the invention encompasses the polynucleotide comprising the nucleic acid of SEQ ID NO:2, as shown in FIGS. 1A, 1B, and 1C.

It will be appreciated by those skilled in the art that as a result of the degeneracy of the genetic code, a multitude of nucleotide sequences encoding EBPH, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring EBPH, and all such variations are to be considered as being specifically disclosed.

Although nucleotide sequences which encode EBPH and its variants are preferably capable of hybridizing to the nucleotide sequence of the naturally occurring EBPH under appropriately selected conditions of stringency, it may be advantageous to produce nucleotide sequences encoding EBPH or its derivatives possessing a substantially different codon usage. Codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding EBPH and its derivatives, without altering the encoded amino acid sequences, include the production of RNA transcripts having more desirable properties, such as a greater half-life, than transcripts produced from the naturally occurring sequence.

The invention also encompasses production of a DNA sequence, or portions thereof, which encode EBPH and its derivatives, entirely by synthetic chemistry. After production, the synthetic gene may be inserted into any of the many available DNA vectors and cell systems using reagents that are well known in the art at the time of the filing of this application. Moreover, synthetic chemistry may be used to introduce mutations into a sequence encoding EBPH or any portion thereof.

Also encompassed by the invention are polynucleotide sequences that are capable of hybridizing to the claimed nucleotide sequences, and in particular, those shown in SEQ ID NO:2, under various conditions of stringency. Hybridization conditions are based on the melting temperature (Tm) of the nucleic acid binding complex or probe, as taught in Berger and Kimmel (1987; Methods in Enzymol., Vol. 152, Academic Press, San Diego, Calif.), and may be used at a defined stringency.

Altered nucleic acid sequences encoding EBPH which are encompassed by the invention include deletions, insertions, or substitutions of different nucleotides resulting in a polynucleotide that encodes the same or a functionally equivalent EBPH. The encoded protein may also contain deletions, insertions, or substitutions of amino acid residues which produce a silent change and result in a functionally equivalent EBPH. Deliberate amino acid substitutions may be made on the basis of similarity in polarity, charge, solubility, hydrophobicity, hydrophilicity, and/or the amphipathic nature of the residues as long as the biological activity of EBPH is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; phenylalanine and tyrosine.

Also included within the scope of the present invention are alleles encoding EBPH. As used herein, an "allele" or "allelic sequence" is an alternative form of the gene which may result from at least one mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of amino acids. Each of these types of changes may occur alone, or in combination with the others, one or more times in a given sequence.

Methods for DNA sequencing which are well known and generally available in the art may be used to practice any embodiments of the invention. The methods may employ such enzymes as the Klenow fragment of DNA polymerase I, Sequenase® (US Biochemical Corp, Cleveland, Ohio), Taq polymerase (Perkin Elmer), thermostable T7 polymerase (Amersham, Chicago, IL), or combinations of recombinant polymerases and proofreading exonucleases such as the ELONGASE Amplification System marketed by Gibco BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI 377 DNA sequencers (Perkin Elmer).

The polynucleotide sequence encoding EBPH may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Gobinda, et al. (1993) PCR Methods Applic. 2:318–322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using OLIGO® 4.06 primer analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown portion of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PromoterFinder™ libraries to walk in genomic DNA (Clontech, Palo Alto, Calif.). This process avoids the need to screen libraries and may be useful in finding intron/exon junctions.

When screening for full-length cDNAs, it is preferable to use libraries that have been size-selected to include larger cDNAs. Also, random-primed libraries are preferable in that they will contain more sequences which contain the 5' and upstream regions of genes. Use of a randomly primed library may be especially preferable for situations in which an oligo d(T) library does not yield a full-length cDNA. Genomic libraries may be useful for extension of sequence into the 5' and 3' non-translated regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. Genotyper™ and Sequence Navigator™ from Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode EBPH, or fusion proteins or functional equivalents thereof, may be used in recombinant DNA molecules to direct expression of EBPH in appropriate host cells. Due to the inherent degeneracy of the genetic code, other DNA sequences which encode substantially the same or a functionally equivalent amino acid sequence may be produced and; these sequences may be used to clone and express EBPH.

As will be understood by those of skill in the art, it may be advantageous to produce EBPH-encoding nucleotide sequences possessing non-naturally occurring codons. For example, codons preferred by a particular prokaryotic or eukaryotic host can be selected to increase the rate of EBPH expression or to produce a recombinant RNA transcript having desirable properties, such as a half-life which is longer than that of a transcript generated from the naturally occurring sequence.

The nucleotide sequences of the present invention can be engineered using methods generally known in the art in order to alter the EBPH coding sequence for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequence. For example, site-directed mutagenesis may be used to insert new restriction sites, alter glycosylation patterns, to change codon preference, to produce splice variants, or other mutations, and so forth.

In another embodiment of the invention, a natural, modified, or recombinant polynucleotide encoding EBPH may be ligated to a heterologous sequence to encode a fusion protein. For example, to screen peptide libraries for inhibitors of EBPH activity, it may be useful to encode a chimeric EBPH protein that can be recognized by a commercially available antibody. A fusion protein may also be engineered to contain a cleavage site located between an EBPH encoding sequence and the heterologous protein sequence, so that the EBPH may be cleaved and purified away from the heterologous moiety.

In another embodiment, the coding sequence of EBPH may be synthesized, in whole or in part, using chemical methods well known in the art (see Caruthers, M. H. et al. (1980) Nucl. Acids Res. Symp. Ser. 215–223; Horn, T. et al. (1980) Nucl. Acids Res. Symp. Ser. 225–232). Alternatively, the protein itself may be produced using chemical methods to synthesize the EBPH amino acid sequence, or a portion thereof. For example, peptide synthesis can be performed using various solid-phase techniques (Roberge, et al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) *Proteins, Structures and Molecular Principles*, WH Freeman and Co., New York, N.Y.). The composition of the synthetic peptides may be confirmed by amino acid analysis or sequencing (e.g., the Edman degradation procedure; Creighton, supra). Additionally, the amino acid sequence of EBPH, or any part thereof, may be altered during direct synthesis and/or combined using chemical methods with sequences from other proteins, or any part thereof, to produce a variant polypeptide.

In order to express a biologically active EBPH, the nucleotide sequence encoding EBPH or functional equivalents, may be inserted into an appropriate expression vector, i.e., a vector which contains the necessary elements for the transcription and translation of the inserted coding sequence.

Methods which are well known to those skilled in the art may be used to construct expression vectors containing an EBPH coding sequence and appropriate transcriptional or translational controls. These methods include in vitro recombinant DNA techniques, synthetic techniques, and in vivo recombination or genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express a EBPH coding sequence. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or transformed with bacterial expression vectors (e.g., Ti or pBR322 plasmid); or animal cell systems.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, LaJolla, Calif.) or pSport1 (Gibco BRL) and ptrp-lac hybrids, and the like may be used. The baculovirus polyhedrin promoter may be used in insect cells. Promoters or enhancers derived from the genomes of plant cells (e.g., heat shock, RUBISCO, and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding EBPH, vectors based on SV40 or EBV may be used with an appropriate selectable marker.

In bacterial systems, a number of expression vectors may be selected depending upon the use intended for EBPH. For example, when large quantities of EBPH are needed for the induction of antibodies, vectors which direct high level expression of fusion proteins that are readily purified may be used. Such vectors include, but are not limited to, the multifunctional *E. coli* cloning and expression vectors such as Bluescript® (Stratagene), in which the EBPH coding sequence may be ligated into the vector in frame with sequences for the amino-terminal Met and the subsequent 7 residues of β-galactosidase so that a hybrid protein is produced; pIN vectors (Van Heeke, G. et al. (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel, et al. (supra) and Grant, et al. (1987) Methods Enzymol. 153:516–544.

In cases where plant expression vectors are used, the expression of a sequence encoding EBPH may be driven by any of a number of promoters. For example, viral promoters such as the 35S and 19S promoters of CaMV may be used alone or in combination with the omega leader sequence from TMV (Takamatsu et al. (1987) EMBO J. 6:307–311; Brisson et al. (1984) Nature 310:511–514). Alternatively, plant promoters such as the small subunit of RUBISCO or heat shock promoters may be used (Coruzzi et al. (1984) EMBO J. 3:1671–1680; Broglie et al. (1984) Science 224: 838–843; Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196 or Weissbach and Weissbach (1988) *Methods for Plant Molecular Biology*, Academic Press, New York, N.Y.; pp. 421–463).

An insect system may also be used to express EBPH. For example, in one such system, *Autographa californica* nuclear polyhedrosis virus (AcNPV) is used as a vector to express foreign genes in *Spodoptera frugiperda* cells or in *Trichoplusia larvae*. The EBPH coding sequence may be cloned into a non-essential region of the virus, such as the polyhedrin gene, and placed under control of the polyhedrin promoter. Successful insertion of EBPH will render the polyhedrin gene inactive and produce recombinant virus lacking coat protein. The recombinant viruses may then be used to infect, for example, *S. frugiperda* cells or *Trichoplusia larvae* in which EBPH may be expressed (Smith et al. (1983) J. Virol 46:584; Engelhard, E. K. et al. (1994) Proc. Natl. Acad. Sci. 91:3224–3227).

In mammalian host cells, a number of viral-based expression systems may be utilized. In cases where an adenovirus is used as an expression vector, an EBPH coding sequence may be ligated into an adenovirus transcription/translation complex consisting of the late promoter and tripartite leader sequence. Insertion in a non-essential E1 or E3 region of the viral genome may be used to obtain a viable virus which is capable of expressing EBPH in infected host cells (Logan and Shenk (1984) Proc. Natl. Acad. Sci. 81:3655–3659). In addition, transcription enhancers, such as the Rous sarcoma virus (RSV) enhancer, may be used to increase expression in mammalian host cells.

Specific initiation signals may also be used to achieve more efficient translation of a EBPH sequence. Such signals include the ATG initiation codon and adjacent sequences. In cases where sequences encoding EBPH, its initiation codon, and upstream sequences are inserted into the appropriate expression vector, no additional translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162; Bittner et al. (1987) Methods Enzymol. 153:516–544).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and W138, which have specific cellular machinery and characteristic mechanisms for such post-translational activities, may be chosen to ensure the correct modification and processing of the introduced foreign protein.

For long-term, high-yield production of recombinant proteins, stable expression is preferred. For example, cell lines which stably express EBPH may be transformed using expression vectors which may contain viral origins of replication and/or endogenous expression elements and a selectable marker gene on the same or separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in $tk^-$ or $aprt^-$ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate, GUS, and luciferase and its substrate, luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding EBPH is inserted within a marker gene sequence, recombinant cells containing sequences encoding EBPH can be identified by the absence of marker gene function. Alternatively, a marker gene can be placed in tandem with an EBPH sequence under the control of a single promoter. Expression of the marker gene in response to induction or selection usually indicates expression of the tandem EBPH as well.

Alternatively, host cells which contain the coding sequence for EBPH and express EBPH may be identified by a variety of procedures known to those of skill in the art. These procedures include, but are not limited to, DNA—DNA or DNA-RNA hybridizations, fluorescent activated cell sorting and protein bioassay or immunoassay techniques which include membrane, solution, or chip based technologies for the detection and/or quantification of the nucleic acid or protein.

The presence of the polynucleotide sequence encoding EBPH can be detected by DNA—DNA or DNA-RNA hybridization or amplification using probes or portions or fragments of polynucleotides encoding EBPH. Nucleic acid amplification based assays involve the use of oligonucleotides or oligomers based on the EBPH-encoding sequence to detect transfectants containing DNA or RNA encoding EBPH. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides, which can be used as a probe or amplimer.

A variety of protocols for detecting and measuring the expression of EBPH, using either polyclonal or monoclonal antibodies specific for the protein are known in the art. Examples include enzyme-linked immunosorbent assay (ELISA), radioimmunoassay (RIA), and fluorescent activated cell sorting (FACS). A two-site, monoclonal-based immunoassay utilizing monoclonal antibodies reactive to two non-interfering epitopes on EBPH is preferred, but a competitive binding assay may be employed. These and other assays are described, among other places, in Hampton et al. (1990, *Serological Methods, a Laboratory Manual*, APS Press, St Paul, Minn.) and Maddox D E et al. (1983) J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding EBPH include oligolabeling, nick translation, end-labeling or PCR amplification using a labeled nucleotide. Alternatively, the sequence encoding EBPH, or any portion of it, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia Upjohn, (Kalamazoo, Mich.); Promega (Madison, Wis.); and U.S. Biochemical Corp., (Cleveland, Ohio)). Suitable reporter molecules or labels, which may be used, include radionuclides, enzymes, fluorescent, chemiluminescent, or chromogenic agents as well as substrates, cofactors, inhibitors, magnetic particles, and the like.

Host cells transformed with a nucleotide sequence encoding EBPH may be cultured under conditions suitable for the expression and recovery of the encoded protein from cell culture. The protein produced by a recombinant cell may be secreted or contained intracellularly depending on the sequence and/or the vector used. As will be understood by those of skill in the art, expression vectors containing polynucleotides which encode EBPH may be designed to contain signal sequences which direct secretion of EBPH through a prokaryotic or eukaryotic cell membrane. Other recombinant constructions may be used to join sequences encoding EBPH to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle Wash.). The inclusion of cleavable linker sequences such as those specific for Factor XA or enterokinase (Invitrogen, San Diego, Calif.) between the purification domain and EBPH may be used to facilitate purification. One such expression vector which may be used provides for expression of a fusion protein containing EBPH and a nucleic acid encoding 6 histidine residues followed by thioredoxin and an enterokinase cleavage site. The histidine residues facilitate purification on IMIAC (immobilized metal ion affinity chromatography as described in Porath, J. et al. (1992; Protein Exp.Purif. 3:263–281) while the enterokinase cleavage site provides a means for purifying EBPH from the fusion protein. A discussion of vectors which contain fusion proteins is provided in Kroll, D. J. et al. (1993; DNA Cell Biol. 12:441–453).

In addition to recombinant production, fragments of EBPH may be produced by direct peptide synthesis using solid-phase techniques (cf Stewart et al. (1969) *Solid-Phase Peptide Synthesis*, W.H. Freeman Co., San Francisco, Calif.; Merrifield J. (1963) J. Am. Chem. Soc. 85:2149–2154). In vitro protein synthesis may be performed using manual techniques or by automation. Automated synthesis may be achieved, for example, using Applied Biosystems 431A Peptide Synthesizer (Perkin Elmer). Various fragments of EBPH may be chemically synthesized separately and combined using chemical methods to produce the full length molecule.

Therapeutics

In another embodiment of the invention, EBPH or fragments thereof may be used for therapeutic purposes.

Chemical and structural homology exists among EBPH and the eosinophil granule MBPs from human and guinea pig. In addition, northern analysis demonstrates that mRNA encoding full-length EBPH was found only in a library constructed from pooled human umbilical cord blood cells cultured in the presence of IL-5 (UCMCL5T01). Since umbilical cord blood is a rich source of stem cells and IL-5 is a potent eosinophilic differentiation factor, EBPH is believed to function as an eosinophil granule protein. Furthermore, a significant proportion of the cDNA clones in the UCMCL5TO 1 library encode eosinophil-specific proteins. It must be noted, however, that naturally occurring expression of EBPH is not necessarily limited to eosinophils.

From the homology and expression information provided above, it appears that EBPH plays a role in host defense mechanisms against parasitic and bacterial infections. Accordingly, in another embodiment of the invention, EBPH or derivatives thereof may be used as cytolytic agents in the treatment of such infections.

In another embodiment of the invention, EBPH may be used as a cytolytic agent against cancer cells. Control of EBPH activity as a novel approach to cancer treatment may be especially useful in combination therapy with other, conventional chemotherapeutic agents. Such combinations of therapeutic agents having different cellular mechanisms of action often have synergistic effects allowing the use of lower effective doses of each agent and lessening side effects.

Eosinophil-associated diseases and conditions, including type I allergic reactions, vary in severity. Allergic rhinitis, which affects a large segment of the population, has severe economic impact. Anaphylaxis is a major complication of allergic reactions which in many instances is fatal. Asthma is a chronic disease of the airways characterized by mucus hypersecretion as well as bronchial inflammation, edema, and hyperresponsiveness resulting in increased bronchoconstriction. Atopic dermatitis is an allergic skin disease associated with high eosinophil levels which result in skin lesions. Hypereosinophilic syndrome and eosinophilic endomyocardial disease may lead to severe cardiac tissue damage and cardiac failure. Graft-vs.-host disease is also associated with high eosinophil accumulation and degranulation.

Therefore, in another embodiment of the invention, vectors expressing antisense and antagonists or inhibitors which block or modulate the effect of EBPH may be used in those situations where such inhibition or modulation is therapeutically desirable. Such situations may include diseases and conditions with which eosinophil accumulation and granule release are involved, including the diseases discussed above. In such situations, EBPH released from eosinophils may promote or exacerbate inflammation and tissue damage. EBPH may also induce further eosinophil degranulation and thus act as an autocrine mediator in the pathogenesis of eosinophil-associated diseases.

Antagonists of EBPH may be produced using methods which are generally known in the art. In one aspect, proEBPH may be useful as an inhibitor of EBPH-associated functions, including, but not limited to, those associated with the activation and degranulation of eosinophils, basophils, and neutrophils, including histamine and superoxide release. To prevent the processing of administered proEBPH into mature EBPH in vivo, variants of EBPH may be produced which contain at least one mutation in SEQ ID NO:1 located at or about the pro-mature domain boundary, said boundary located approximately at amino acid residues 108 and 109 of SEQ ID NO:1.

In another aspect of the invention, the isolated-EBPH pro domain, comprising amino acid residues 17 to 108 of SEQ ID NO:1, may likewise be useful as an inhibitor of mature EBPH. The pro domain may be particularly useful in preventing or treating EBPH-associated tissue damage. Most particularly, the EBPH pro domain may be administered topically to prevent or to treat tissue damage associated with EBPH. Such applications may include, but are not limited to: inhalants for the prevention or treatment of bronchial hyperreactivity and tissue damage associated with asthma; nose drops for the prevention or treatment of nasal tissue irritation associated with allergic rhinitis; and ointments for the prevention or treatment of skin lesions associated with atopic dermatitis.

In another aspect, antibodies which are specific for EBPH may be used as an agonist, antagonist, or as part of a targeting or delivery mechanism so as to bring a pharmaceutical agent to cells or tissues which express EBPH.

The antibodies may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, and humans, may be immunized by injection with EBPH or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the peptides, fragments, or oligopeptides used to induce antibodies to EBPH have an amino acid sequence consisting of at least five amino acids, and more preferably at least 10 amino acids. It is also preferable that they are identical to a portion of the amino acid sequence of the natural protein, and they may contain the entire amino acid sequence of a small, naturally occurring molecule. Short stretches of EBPH amino acids may be fused with those of another protein such as keyhole limpet hemocyanin and antibody produced against the chimeric molecule.

Monoclonal antibodies to EBPH may be prepared using any technique which provides for the production of antibody molecules by continuous cell lines in culture. These include, but are not limited to, the hybridoma technique, the human B-cell hybridoma technique, and the EBV-hybridoma technique (Koehler et al. (1975) Nature 256:495–497; Kosbor et al. (1983) Immunol. Today 4:72; Cote et al. (1983) Proc. Natl. Acad. Sci. 80:2026–2030; Cole et al. (1985) *Monoclonal Antibodies and Cancer Therapy*, Alan R. Liss Inc., New York, N.Y., pp. 77–96).

In addition, techniques developed for the production of "chimeric antibodies", the splicing of mouse antibody genes to human antibody genes to obtain a molecule with appropriate antigen specificity and biological activity can be used (Morrison et al. (1984) Proc. Natl. Acad. Sci. 81:6851–6855; Neuberger et al. (1984) Nature 312:604–608; Takeda et al. (1985) Nature 314:452–454). Alternatively, techniques described for the production of single chain antibodies may be adapted, using methods known in the art, to produce EBPH-specific single chain antibodies. Antibodies with related specificity but of distinct idiotypic composition may be generated by chain shuffling from random combinatorial immunoglobulin libraries (Burton D. R. (1991) Proc. Natl. Acad. Sci. 88:11120–3).

Antibodies may also be produced by inducing in vivo production in the lymphocyte population or by screening recombinant immunoglobulin libraries or panels of highly specific binding reagents as disclosed in the literature (Orlandi et al. (1989) Proc. Natl. Acad. Sci. 86: 3833–3837; Winter, G. et al. (1991) Nature 349:293–299).

Antibody fragments which contain specific binding sites for EBPH may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 256:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between EBPH and its specific antibody. A two-site, monoclonal-based immunoassay utilizing monoclonal antibodies reactive to two non-interfering epitopes on a specific EBPH protein is preferred, but a competitive binding assay may also be employed (Maddox (1983), supra).

In another embodiment of the invention, the polynucleotides encoding EBPH, or any fragment thereof or antisense sequences, may be used for therapeutic purposes. In one aspect, antisense to the polynucleotide encoding EBPH may be used in situations in which it would be desirable to block the synthesis of the protein. In particular, cells may be transformed with antisense sequences to polynucleotides encoding EBPH. Thus, antisense sequences may be used to prevent EBPH-associated tissue damage, or to achieve regulation of gene function. Such technology is now well known in the art, and sense or antisense oligomers, or larger fragments, can be designed from various locations along the coding or control regions.

Expression vectors derived from retroviruses, adenovirus, herpes or vaccinia viruses, or from various bacterial plasmids, may be used for delivery of nucleotide sequences to the targeted organ, tissue, or cell population. Methods which are well known to those skilled in the art can be used to construct recombinant vectors which will express antisense polynucleotides of the gene encoding EBPH. See, for example, the techniques described in Sambrook et al. (supra) and Ausubel et al. (supra).

Genes encoding EBPH can be turned off by transfecting a cell or tissue with expression vectors which express high levels of a polynucleotide or fragment thereof which encodes EBPH. Such constructs may be used to introduce untranslatable sense or antisense sequences into a cell. Even in the absence of integration into the DNA, such vectors may continue to transcribe RNA molecules until all copies are disabled by endogenous nucleases. Transient expression may last for a month or more with a non-replicating vector and even longer if appropriate replication elements are part of the vector system.

As mentioned above, modifications of gene expression can be obtained by designing antisense molecules, DNA, RNA, or PNA, to the control regions of the gene encoding EBPH, i.e., the promoters, enhancers, and introns. Oligonucleotides derived from the transcription initiation site, e.g., between positions −10 and +10 from the ATG start site, are preferred. The antisense molecules may also be designed to block translation of mRNA by preventing the transcript from binding to ribosomes. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I Carr, *Molecular and Immunologic Approaches*, Futura Publishing Co., Mt. Kisco, N.Y.).

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding EBPH.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding EBPH. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Methods for introducing vectors into cells or tissues include those methods discussed above. These methods are equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods which are well known in the art.

Any of the therapeutic methods described above may be applied to any suitable subject including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of EBPH, antibodies to EBPH, mimetics, agonists, antagonists, or inhibitors of EBPH. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers, well known in the art, in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acids, etc. Salts tend to be more soluble in aqueous or other protonic solvents than are the corresponding free base forms. In other cases, the preferred preparation may be a lyophilized powder which may contain any or all of the following:

1 mM-50 mM histidine, 0.1%–2% sucrose, and

2%–7% mannitol at a pH range of 4.5 to 5.5 that is/are combined with buffer prior to use.

After pharmaceutical compositions have been prepared, they can be placed in an appropriate container and labeled for treatment of an indicated condition. For administration of EBPH, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example EBPH or fragments thereof, agonists antibodies to EBPH or agonists, antagonists, or inhibitors of EBPH, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio of toxic to therapeutic effects is the therapeutic index, which can be expressed as the ratio LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject who requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which are specific for EBPH may be used for the diagnosis of conditions or diseases characterized by expression of EBPH, or in assays to monitor patients being treated with EBPH, agonists, antagonists or inhibitors. The antibodies useful for diagnostic purposes may be prepared in the same manner as those described above for therapeutics. Diagnostic assays for EBPH include methods which utilize the antibody and a label to detect EBPH in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring EBPH are known in the art and provide a basis for diagnosing altered or abnormal levels of EBPH expression. Normal or standard values for EBPH expression are established by combining body fluids or cell extracts taken from normal mammalian subjects, preferably human, with antibody to EBPH under conditions suitable for complex formation. The amount of standard complex formation may be quantified by various methods, preferably by photometric means.

Quantities of EBPH expressed in subject, control, and disease samples from biopsied tissues are compared with the standard values. Deviation between standard and subject values establishes the parameters for diagnosing disease.

In another embodiment of the invention, the polynucleotides encoding EBPH may be used for diagnostic purposes. The polynucleotides which may be used include oligonucleotide sequences, antisense RNA and DNA molecules, and PNAs. The polynucleotides may be used to detect and quantitate gene expression in biopsied tissues in which expression of EBPH may be correlated with disease. The diagnostic assay may be used to distinguish between absence, presence, and excess expression of EBPH, and to monitor regulation of EBPH levels during therapeutic intervention.

In one aspect, hybridization with PCR probes which are capable of detecting polynucleotide sequences, including genomic sequences, encoding EBPH or closely related molecules, may be used to identify nucleic acid sequences which encode EBPH. The specificity of the probe, whether it is made from a highly specific region, e.g., 10 unique nucleotides in the 5' regulatory region, or a less specific region, e.g., especially in the 3' region, and the stringency of the hybridization or amplification (maximal, high, intermediate, or low) will determine whether the probe identifies only naturally occurring sequences encoding EBPH, alleles, or related sequences.

Probes may also be used for the detection of related sequences, and should preferably contain at least 50% of the nucleotides from any of these EBPH encoding sequences. The hybridization probes of the subject invention may be derived from the nucleotide sequence of SEQ ID NO:2 or from genomic sequence including promoter, enhancer elements, and introns of the naturally occurring EBPH.

Other means for producing specific hybridization probes for DNAs encoding EBPH include the cloning of nucleic acid sequences encoding EBPH or EBPH derivatives into vectors for the production of mRNA probes. Such vectors are known in the art, commercially available, and may be used to synthesize RNA probes in vitro by means of the addition of the appropriate RNA polymerases and the appropriate radioactively labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding EBPH may be used for the diagnosis of conditions or diseases which are associated with expression of EBPH. Examples of such conditions or diseases include type I allergic reactions, parasitic infections, and eosinophilias. In addition, proEBPH in placenta may be complexed with other pregnancy-associated molecules such as PAPP-A and angiotensinogen and thus may be useful in the diagnosis of pregnancy-associated conditions. The polynucleotide sequences encoding EBPH may be used in Southern or northern analysis, dot blot, or other membrane-based technologies; in PCR technologies; in dip stick, pin, chip, and ELISA assays of fluids or tissues from patient biopsies to detect altered EBPH expression. Such qualitative or quantitative methods are well known in the art.

In order to provide a basis for the diagnosis of disease associated with expression of EBPH, a normal or standard profile for expression is established. This may be accomplished by combining body fluids or cell extracts taken from normal subjects, either animal or human, with a sequence, or a fragment thereof, which encodes EBPH, under conditions suitable for hybridization or amplification. Standard hybridization may be quantified by comparing the values obtained from normal subjects with a dilution series of EBPH measured in the same experiment, where a known amount of a substantially purified EBPH is used. Standard values obtained from normal samples may be compared with values obtained from samples from patients who are symptomatic for disease associated with EBPH. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

Additional diagnostic uses for oligonucleotides encoding EBPH may involve the use of PCR. Such oligomers may be chemically synthesized, generated enzymatically, or produced from a recombinant source. Oligomers will preferably consist of two nucleotide sequences, one with sense orientation (5'->3') and another with antisense (3'<-5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of EBPH include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 212:229–236.) The speed of quantitation of multiple samples may be accelerated by running the assay in an ELISA format where the oligomer of interest is presented in various dilutions and a spectrophotometric or colorimetric response gives rapid quantitation.

In another embodiment of the invention, the nucleic acid sequence which encodes EBPH may also be used to generate hybridization probes which are useful for mapping the naturally occurring genomic sequence. The sequence may be mapped to a particular chromosome or to a specific region of the chromosome using well known techniques. Such techniques include FISH, FACS, or artificial chromosome constructions, such as yeast artificial chromosomes, bacterial artificial chromosomes, bacterial P1 constructions or single chromosome cDNA libraries as reviewed in Price, C. M. (1993) Blood Rev. 7:127–134, and Trask, B. J. (1991) Trends Genet. 7:149–154.

FISH (as described in Verma et al. (1988) Human Chromosomes: *A Manual of Basic Techniques*, Pergamon Press, New York, N.Y.) may be correlated with other physical chromosome mapping techniques and genetic map data. Examples of genetic map data can be found in the 1994 Genome Issue of Science (265:198 If). Correlation between the location of the gene encoding EBPH on a physical chromosomal map and a specific disease (or predisposition to a specific disease) may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, EBPH, its catalytic or immunogenic fragments or oligopeptides thereof, can be used for screening libraries of compounds in any of a variety of drug screening techniques. The fragment employed in such a test may be free in solution, affixed to a solid support, borne on a cell surface, or located intracellularly. The formation of binding complexes, between EBPH and the agent being tested, may be measured.

Another technique for drug screening which may be used provides for high throughput screening of compounds having suitable binding affinity to the protein of interest as described in published PCT application WO84/03564. In this method, as applied to EBPH, large numbers of different small test compounds are synthesized on a solid substrate, such as plastic pins or some other surface. The test compounds are reacted with EBPH, or fragments thereof, and washed. Bound EBPH is then detected by methods well known in the art. Purified EBPH can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding EBPH specifically compete with a test compound for binding EBPH. In this manner, the antibodies can be used to detect the presence of any peptide which shares one or more antigenic determinants with EBPH.

In additional embodiments, the nucleotide sequences which encode EBPH may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I Construction of cDNA Libraries

Mononuclear cells were obtained from the umbilical cord blood of 12 individuals and were cultured in the presence of IL-5 for 12 days. The cells were homogenized and lysed using a Brinkmann Homogenizer Polytron PT-3000 (Brinkmann Instruments, Westbury, N.J.) in guanidinium isothiocyanate solution. The lysate was centrifuged over a 5.7 M CsCl cushion using an Beckman SW28 rotor in a Beckman L8–70M Ultracentrifuge (Beckman Instruments) for 18 hours at 25,000 rpm at ambient temperature. The RNA was extracted with acid phenol pH 4.7, precipitated using 0.3 M sodium acetate and 2.5 volumes of ethanol, resuspended in RNAse-free water, and DNAse treated at 37° C. The RNA extraction was repeated with acid phenol pH 4.7 and precipitated with sodium acetate and ethanol as before. The mRNA was then isolated using the Qiagen Oligotex kit (QIAGEN, Inc., Chatsworth, Calif.) and used to construct the cDNA library.

The mRNA was handled according to the recommended protocols in the SuperScript Plasmid System for cDNA Synthesis and Plasmid Cloning (Cat. #18248–013, Gibco/BRL).

The commercial plasmid pSPORT 1™ (Gibco/BRL) was digested with EcoR I restriction enzyme (New England Biolabs, Beverley, Mass.). The overhanging ends of the plasmid were filled in using Klenow enzyme (New England Biolabs) and 2'-deoxynucleotide 5'-triphosphates (dNTPs). The plasmid was self-ligated and transformed into the bacterial host, E. coli strain JM 109. An intermediate plasmid produced by the bacteria failed to digest with EcoR I confirming the desired loss of the EcoR I restriction site.

This intermediate plasmid (pSPORT 1-ΔRI) was then digested with Hind III restriction enzyme (New England Biolabs) and the overhang was filled in with Klenow and dNTPs. A 10-mer linker of sequence 5' . . . CGGAATTCCG . . . 3' was phosphorylated and ligated onto the blunt ends. The product of the ligation reaction was digested with EcoR I and self-ligated. Following transformation into JM109 host cells, plasmids were isolated and screened for the digestibility with EcoR I but not with Hind III. A single colony which met this criteria was designated pINCY 1. The plasmid produced by this colony was sequenced and found to contain several copies of the 10-mer linker. These extra linkers did not present a problem as they were eliminated when the vector was prepared for cloning.

The plasmid was tested for its ability to incorporate cDNAs from a library prepared using Not I and EcoR I restriction enzymes. Several clones were sequenced and a single clone containing an insert of approximately 0.8 kb was selected to prepare a large quantity of the plasmid for library production. After digestion with Not I and EcoR I, the plasmid and the cDNA insert were isolated on an agarose gel and the vector was purified on a QIAQuick™ (QIAGEN, Inc.) column for use in library construction.

cDNAs were fractionated on a Sepharose CL4B column (Cat. #275105–01, Pharmacia), and those cDNAs exceeding 400 bp were ligated into pSport I. The plasmid pSport I was subsequently transformed into DH5a™ competent cells (Cat. #18258–012, Gibco/BRL).

II Isolation and Sequencing of cDNA Clones

Plasmid DNA was released from the cells and purified using the REAL Prep 96 Plasmid Kit for Rapid Extraction Alkaline Lysis Plasmid Minipreps (Catalog #26173, QIAGEN, Inc.). This kit enabled the simultaneous purification of 96 samples in a 96-well block using multi-channel reagent dispensers. The recommended protocol was employed except for the following changes: 1) the bacteria were cultured in 1 ml of sterile Terrific Broth (Catalog #22711, Life Technologies) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger et al. (1975, J. Mol. Biol. 94:441f), using a Hamilton Micro Lab 2200 (Hamilton, Reno, Nev.) in combination with Peltier Thermal Cyclers (PTC200 from MJ Research, Watertown, Mass.) and Applied Biosystems 377 DNA Sequencing Systems; and the reading frame was determined.

Most of the sequences disclosed herein were sequenced according to standard ABI protocols, using ABI kits (Cat. Nos. 79345, 79339, 79340, 79357, 79355). The solution volumes were used at 0.25×–1.0× concentrations. Some of the sequences disclosed herein were sequenced using different solutions and dyes which, unless otherwise noted, came from Amersham Life Science (Cleveland, Ohio).

Stock solutions were prepared with HPLC water. The following solutions were each mixed by vortexing for 2 min: 1) Tris-EDTA (TE) Buffer was prepared by adding 49 ml water to 1 ml 50× Tris-EDTA concentrate, and 2) 10% Reaction Buffer was prepared by adding 45 ml water to 5 ml Concentrated Thermo Sequenase (TS) Reaction Buffer.

Energy transfer (ET) primers (0.2 µM) were prepared in the following manner. Each primer tube was centrifuged prior to opening to assure that all primer powder was on the bottom of the tube. After each solubilization step, the mixture was vortexed for 2 min and then centrifuged for about 10 sec in a table-top centrifuge. 1 ml of 1×TE was added to each primer powder; adenine and cytosine dissolved primers (5-carboxyrhodamine-6G (R6G) and 6-carboxyfluorescein (FAM), respectively), were diluted with 9 ml 1×TE. Guanine and thymine dyes (N,N,N',N"-tetramethyl-6-carboxyrhodamine (TAM) and 6-carboxy-X-rhodamine (ROX), respectively) were diluted with 19 ml 1×TE.

The sequencing reaction ready mix was prepared as follows: 1) nucleotides A and C (8 ml of each) were added to 6 ml ET primer and 18 ml TS reaction buffer; and 2) nucleotides G and T (8 ml of each) were added to 6 ml ET primer and 18 ml TS reaction buffer. After vortexing for 2 min and centrifuging for 20 sec, the resulting solution was divided into tubes in volumes of 8 ml per tube in order to make 1× (A,C) and 2× (G,T) solutions.

Prior to thermal cycling, each nucleotide was individually mixed with DNA template in the following proportions:

| Reagent | A(μL) | C(μL) | G(μL) | T(μL) |
|---|---|---|---|---|
| Reaction ready premix | 2 | 2 | 4 | 4 |
| DNA template | 1 | 1 | 2 | 2 |
| Total Volume | 3 | 3 | 6 | 6 |

These solutions were subjected to the usual thermal cycling:
1. Rapid thermal ramp to 94° C. (94° C. for 20 sec)*
2. Rapid thermal ramp to 50° C. (50° C. for 40 sec)*
3. Rapid thermal ramp to 68° C. (68° C. for 60 sec)*
   Steps 1, 2, and 3 were repeated for 15 cycles
4. Rapid thermal ramp to 94° C. (94° C. for 20 sec)**
5. Rapid thermal ramp to 68° C. (68° C. for 60 sec)**
   Steps 4 and 5 were repeated for 15 cycles
6. Rapid thermal ramp to 4° C. and hold until ready to combine.

After thermal cycling, the A, C, G, and T reactions were combined with each DNA template. Then, 50 μL 100% ethanol was added and the solution was spun at 4° C. for 30 min. The supernatant was decanted and the pellet was rinsed with 100 μL 70% ethanol. After being spun for 15 min the supernatant was discarded and the pellet was dried for 15 min under vacuum. The DNA sample was dissolved in 3 μL of formaldehyde/50 mM EDTA. The resulting samples were loaded on wells in volumes of 2 μL per well for sequencing in ABI sequencers.

III Homology Searching of cDNA Clones and Their Deduced Proteins

Each cDNA was compared to sequences in GenBank using a search algorithm developed by Applied Biosystems and incorporated into the INHERIT™ 670 Sequence Analysis System. In this algorithm, Pattern Specification Language (TRW Inc, Los Angeles, CA) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT-670 Sequence Analysis System using the methods similar to those used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul SF (1993) J. Mol. Evol. 36:290–300; Altschul et al. (1990) J. Mol. Biol. 215:403–410), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul S. F. 1993 and 1990, supra) are used to search for identical or related molecules in nucleotide databases such as GenBank or the LEFESEQ™ database (Incyte Pharmaceuticals, Inc.). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding EBPH occurs. Abundance and percentage abundance are also reported. Abundance directly reflects the number of times a particular transcript is represented in a cDNA library, and percentage abundance is abundance divided by the total number of sequences examined in the cDNA library.

V Extension of EBPH-Encoding Polynucleotides to Full Length or to Recover Regulatory Elements Full length EBPH-encoding nucleic acid sequence (SEQ ID NO:2) is used to design oligonucleotide primers for extending a partial nucleotide sequence to full length or for obtaining 5' sequences from genomic libraries. One primer is synthesized to initiate extension in the antisense direction (XLR) and the other is synthesized to extend sequence in the sense direction (XLF). Primers are used to facilitate the extension of the known sequence "outward" generating amplicons containing new, unknown nucleotide sequence for the region of interest. The initial primers are designed from the cDNA using OLIGO® 4.06 (National Biosciences), or another appropriate program, to be 22–30 nucleotides in length, to have a GC content of 50% or more, and to anneal to the target sequence at temperatures about 680–72° C. Any stretch of nucleotides which would result in hairpin structures and primer—primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; M.J. Research, Watertown, Mass.) and the following parameters:

Step 1 94° C. for 1 min (initial denaturation)
Step 2 65° C. for 1 min
Step 3 68° C. for 6 min
Step 4 94° C. for 15 sec
Step 5 65° C. for 1 min
Step 6 68° C. for 7 min
Step 7 Repeat step 4–6 for 15 additional cycles
Step 8 94° C. for 15 sec
Step 9 65° C. for 1 min
Step 10 68° C. for 7:15 min
Step 11 Repeat step 8–10 for 12 cycles
Step 12 72° C. for 8 min
Step 13 4° C. (and holding)

A 5–10 μl aliquot of the reaction mixture is analyzed by electrophoresis on a low concentration (about 0.6–0.8%) agarose mini-gel to determine which reactions were successful in extending the sequence. Bands thought to contain the largest products are selected and removed from the gel. Further purification involves using a commercial gel extraction method such as QIAQuick™ (QIAGEN Inc., Chatsworth, Calif.). After recovery of the DNA, Klenow enzyme is used to trim single-stranded, nucleotide overhangs creating blunt ends which facilitate religation and cloning.

After ethanol precipitation, the products are redissolved in 13 μl of ligation buffer, 1 μl T4-DNA ligase (15 units) and 1 μl T4 polynucleotide kinase are added, and the mixture is incubated at room temperature for 2–3 hours or overnight at 16° C. Competent E. coli cells (in 40 μl of appropriate media) are transformed with 3 μl of ligation mixture and cultured in 80 μl of SOC medium (Sambrook et al., supra). After incubation for one hour at 37° C., the whole transformation mixture is plated on Luria Bertani (LB)-agar (Sambrook et al., supra) containing 2xCarb. The following day, several colonies are randomly picked from each plate and cultured in 150 μl of liquid LB/2xCarb medium placed in an individual well of an appropriate, commercially-available, sterile 96-well microtiter plate. The following day, 5 μl of each overnight culture is transferred into a non-sterile 96-well plate and after dilution 1:10 with water, 5 μl of each sample is transferred into a PCR array.

For PCR amplification, 18 μl of concentrated PCR reaction mix (3.3x) containing 4 units of rTth DNA polymerase, a vector primer, and one or both of the gene specific primers used for the extension reaction are added to each well. Amplification is performed using the following conditions:

Step 1 94° C. for 60 sec
Step 2 94° C. for 20 sec
Step 3 55° C. for 30 sec
Step 4 72° C. for 90 sec
Step 5 Repeat steps 2–4 for an additional 29 cycles
Step 6 72° C. for 180 sec
Step 7 4° C. (and holding)

Aliquots of the PCR reactions are run on agarose gels together with molecular weight markers. The sizes of the PCR products are compared to the original partial cDNAs, and appropriate clones are selected, ligated into plasmid, and sequenced.

VI Labeling and Use of Hybridization Probes

Hybridization probes derived from SEQ ID NO:2 are employed to screen cDNAs, genomic DNAs, or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 mCi of [$\gamma$-$^{32}$P] adenosine triphosphate (Amersham, Chicago, Ill.) and T4 polynucleotide kinase (DuPont NEN®, Boston, Mass.). The labeled oligonucleotides are substantially purified with Sephadex G-25 superfine resin column (Pharmacia Upjohn). A portion containing $10_7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham, N. H.). Hybridization is carried out for 16 hours at 40° C. To remove nonspecific signals, blots are sequentially washed at room temperature under increasingly stringent conditions up to 0.1x saline sodium citrate and 0.5% sodium dodecyl sulfate. After XOMAT AR™ film (Kodak, Rochester, N.Y.) is exposed to the blots or the blots are exposed in a PhosphorImager cassette (Molecular Dynamics, Sunnyvale, Calif.), hybridization patterns are compared visually.

VII Antisense Molecules

Antisense molecules to the EBPH-encoding sequence, or any part thereof, is used to inhibit in vivo or in vitro expression of naturally occurring EBPH. Although use of antisense oligonucleotides, comprising about 20 base-pairs, is specifically described, essentially the same procedure is used with larger cDNA fragments. An oligonucleotide based on the coding sequences of EBPH, as shown in FIGS. 1A, 1B, and 1C, is used to inhibit expression of naturally occurring EBPH. The complementary oligonucleotide is designed from the most unique 5' sequence as shown in FIGS. 1A, 1B, and 1C and used either to inhibit transcription by preventing promoter binding to the upstream nontranslated sequence or translation of an EBPH-encoding transcript by preventing the ribosome from binding. Using an appropriate portion of the signal and 5' sequence of SEQ ID NO:2, an effective antisense oligonucleotide includes any 15–20 nucleotides spanning the region which translates into the signal or 5' coding sequence of the polypeptide as shown in FIGS. 1A, 1B, and 1C.

VIII Expression of EBPH

Expression of EBPH is accomplished by subcloning the cDNAs into appropriate vectors and transforming the vectors into host cells. In this case, the cloning vector, pSport, previously used for the generation of the cDNA library is used to express EBPH in E. coli. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of EBPH into the bacterial growth media which can be used directly in the following assay for activity.

IX Demonstration of EBPH Activity

The cytolytic activity of EBPH is assayed by monitoring the release of $^{51}$Cr from cells treated with EBPH. Bronchial epithelial cells, or other suitable cells, are incubated with $^{51}$Cr (Amersham) in an appropriate medium for 1 hour at 37° C. The cells are washed to remove unincorporated $^{51}$Cr and are resuspended. The cytolysis reaction is initiated by addition of EBPH followed by incubation for a predetermined length of time at 37° C. The reaction mixture is centrifuged at 4° C., and radioactivity of an aliquot of the cell-free supernatant is assayed in a gamma scintillation counter. Total cellular $^{51}$Cr content is determined with an aliquot of the reaction mixture lysed in 0.04% Triton X-100, and spontaneous $^{51}$Cr release is determined for cells incubated under the same conditions but in the absence of EBPH.

X Production of EBPH Specific Antibodies

EBPH that is substantially purified using PAGE electrophoresis (Sambrook, supra), or other purification techniques, is used to immunize rabbits and to produce antibodies using standard protocols. The amino acid sequence deduced from SEQ ID NO:2 is analyzed using DNASTAR software (DNASTAR Inc) to determine regions of high immunogenicity and a corresponding oligopolypeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431A using fmoc-chemistry, and coupled to keyhole limpet hemocyanin (KLH, Sigma) by reaction with M-maleimidobenzoyl-N-hydroxysuccinimide ester (MBS; Ausubel et al., supra). Rabbits are immunized with the oligopeptide-KLH complex in complete Freund's adjuvant.

The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring EBPH Using Specific Antibodies

Naturally occurring or recombinant EBPH is substantially purified by immunoaffinity chromatography using antibodies specific for EBPH. An immunoaffinity column is constructed by covalently coupling EBPH antibody to an activated chromatographic resin, such as CnBr-activated Sepharose (Pharmacia Upjohn). After the coupling, the resin is blocked and washed according to the manufacturer's instructions.

Media containing EBPH is passed over the immunoaffinity column, and the column is washed under conditions that allow the preferential absorbance of EBPH (e.g., high ionic strength buffers in the presence of detergent). The column is eluted under conditions that disrupt antibody/EBPH binding (eg, a buffer of pH 2–3 or a high concentration of a chaotrope, such as urea or thiocyanate ion), and EBPH is collected.

XII Identification of Molecules Which Interact with EBPH

EBPH or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled EBPH, washed and any wells with labeled EBPH complex are assayed. Data obtained using different concentrations of EBPH are used to calculate values for the number, affinity, and association of EBPH with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. A method for detecting a target polynucleotide in a sample, said target polynucleotide having a sequence selected from the group consisting of:
   1) the polynucleotide sequence of SEQ ID NO:2,
   2) the polynucleotide sequence complementary to 1), and
   3) the RNA equivalent of 1) or 2), the method comprising:
   a) hybridizing the sample with a probe consisting of at least 20 contiguous nucleotides comprising a sequence complementary to said target polynucleotide in the sample, and which probe specifically hybridizes to said target polynucleotide, under conditions whereby a hybridization complex is formed between said probe and said target polynucleotide, and
   b) detecting the presence or absence of said hybridization complex, and, optionally, if present, the amount thereof.

2. A method of claim 1, wherein the probe consists of at least 60 contiguous nucleotides.

3. A method for detecting a target polynucleotide or fragment thereof in a sample, said target polynucleotide having a sequence selected from the group consisting of:
   1) the polynucleotide sequence of SEQ ID NO:2,
   2) the polynucleotide sequence complementary to 1), and
   3) the RNA equivalent of 1) or 2), the method comprising:
   a) amplifying said target polynucleotide or fragment thereof using polymerase chain reaction amplification, and
   b) detecting the presence or absence of said amplified target polynucleotide or fragment thereof, and, optionally, if present, the amount thereof.

4. A method for screening a compound for effectiveness in altering expression of a target polynucleotide, wherein said target polynucleotide comprises the sequence of SEQ ID NO:2, the method comprising:
   a) exposing a sample comprising the target polynucleotide to a compound, and
   b) detecting altered expression of the target polynucleotide.

\* \* \* \* \*

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
      (A) LENGTH: 225 amino acids
      (B) TYPE: amino acid
      (C) STRANDEDNESS: single
      (D) TOPOLOGY: linear (ii) MOLECULE TYPE: peptide (vii) IMMEDIATE SOURCE:
    (A) LIBRARY: <Unknown>
    (B) CLONE: Consensus (xi) SEQUENCE DESCRIPTION: SEQ ID NO: 1:

```
Met Gln Arg Leu Leu Leu Pro Phe Leu Leu Leu Gly Thr Val Ser
 1               5                  10                  15

Ala Leu His Leu Glu Asn Asp Ala Pro His Leu Glu Ser Leu Glu Thr
            20                  25                  30

Gln Ala Asp Leu Gly Gln Asp Leu Asp Ser Ser Lys Glu Gln Glu Arg
                35                  40                  45

Asp Leu Ala Leu Thr Glu Glu Val Ile Gln Ala Glu Gly Glu Glu Val
 50                  55                  60

Lys Ala Ser Ala Cys Gln Asp Asn Phe Glu Asp Glu Glu Ala Met Glu
 65                  70                  75                  80

Ser Asp Pro Ala Ala Leu Asp Lys Asp Phe Gln Cys Pro Arg Glu Glu
                85                  90                  95

Asp Ile Val Glu Val Gln Gly Ser Pro Arg Cys Lys Thr Cys Arg Tyr
                100                 105                 110

Leu Leu Val Arg Thr Pro Lys Thr Phe Ala Glu Ala Gln Asn Val Cys
                115                 120                 125

Ser Arg Cys Tyr Gly Gly Asn Leu Val Ser Ile His Asp Phe Asn Phe
 130                 135                 140

Asn Tyr Arg Ile Gln Cys Cys Thr Ser Thr Val Asn Gln Ala Gln Val
 145                 150                 155                 160

Trp Ile Gly Gly Asn Leu Arg Gly Trp Phe Leu Trp Lys Arg Phe Cys
                165                 170                 175

Trp Thr Asp Gly Ser His Trp Asn Phe Ala Tyr Trp Ser Pro Gly Gln
                180                 185                 190

Pro Gly Asn Gly Gln Gly Ser Cys Val Ala Leu Cys Thr Lys Gly Gly
                195                 200                 205

Tyr Trp Arg Arg Ala Gln Cys Asp Lys Gln Leu Pro Phe Val Cys Ser
 210                 215                 220

Phe
225
```

(2) INFORMATION FOR SEQ ID NO: 2:

(i) SEQUENCE CHARACTERISTICS:
        (A) LENGTH: 865 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: <Unknown>
        (B) CLONE: Consensus (xi) SEQUENCE DESCRIPTION: SEQ ID NO: 2:

```
GACGGCTCGA GTGGAGGTCT CAGACTCTTG GAAGGGGCTA TACTAGACAC ACAAAGACAG      60

CCCCAAGAAG GACGGTGGAG TAGTGTCCTC GCTAAAAGAC AGTAGATATG CAACGCCTCT     120

TGCTCCTGCC CTTTCTCCTG CTGGGAACAG TTTCTGCTCT TCATCTGGAG AATGATGCCC     180

CCCATCTGGA GAGCCTAGAG ACACAGGCAG ACCTAGGCCA GGATCTGGAT AGTTCAAAGG     240

AGCAGGAGAG AGACTTGGCT CTGACGGAGG AGGTGATTCA GGCAGAGGGA GAGGAGGTCA     300

AGGCTTCTGC CTGTCAAGAC AACTTTGAGG ATGAGGAAGC CATGGAGTCG GACCCAGCTG     360
```

-continued

```
CCTTAGACAA GGACTTCCAG TGCCCCAGGG AAGAAGACAT TGTTGAAGTG CAGGGAAGTC    420

CAAGGTGCAA GACCTGCCGC TACCTATTGG TGCGGACTCC TAAAACTTTT GCAGAAGCTC    480

AGAATGTCTG CAGCAGATGC TACGGAGGCA ACCTTGTCTC TATCCATGAC TTCAACTTCA    540

ACTATCGCAT TCAGTGCTGC ACTAGCACAG TCAACCAAGC CCAGGTCTGG ATTGGAGGCA    600

ACCTCAGGGG CTGGTTCCTG TGGAAGCGGT TTTGCTGGAC TGATGGGAGC CACTGGAATT    660

TTGCTTACTG GTCCCCAGGG CAACCTGGGA ATGGGCAAGG CTCCTGTGTG GCCCTATGCA    720

CCAAAGGAGG TTATTGGCGA CGAGCTCAAT GCGACAAGCA ACTGCCCTTC GTCTGCTCCT    780

TCTAAGCCAG CGGCACGGAG ACCCTGCCAG CAGCTCCCTC CCGTCCCCCA ACCTCTCCTG    840

CTCATAAATC CAGACTTCCC ACAGC                                         865
```

(2) INFORMATION FOR SEQ ID NO: 3:

(i) SEQUENCE CHARACTERISTICS:
        (A) LENGTH: 222 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: 34476

(xi) SEQUENCE DESCRIPTION: SEQ ID NO: 3:

```
Met Lys Leu Pro Leu Leu Ala Leu Leu Phe Gly Ala Val Ser Ala
  1               5                  10                  15

Leu His Leu Arg Ser Glu Thr Ser Phe Glu Thr Pro Leu Gly Ala
                 20                  25                  30

Lys Thr Leu Pro Glu Asp Glu Thr Pro Glu Gln Glu Met Glu Glu
                 35                  40                  45

Thr Pro Cys Arg Glu Leu Glu Glu Glu Glu Trp Gly Ser Gly Ser
 50                  55                  60

Glu Asp Ala Ser Lys Lys Asp Gly Ala Val Glu Ser Ile Ser Val Pro
 65                  70                  75                  80

Asp Met Val Asp Lys Asn Leu Thr Cys Pro Glu Glu Asp Thr Val
                 85                  90                  95

Lys Val Val Gly Ile Pro Gly Cys Gln Thr Cys Arg Tyr Leu Leu Val
                100                 105                 110

Arg Ser Leu Gln Thr Phe Ser Gln Ala Trp Phe Thr Cys Arg Arg Cys
                115                 120                 125

Tyr Arg Gly Asn Leu Val Ser Ile His Asn Phe Asn Ile Asn Tyr Arg
                130                 135                 140

Ile Gln Cys Ser Val Ser Ala Leu Asn Gln Gly Gln Val Trp Ile Gly
145                 150                 155                 160

Gly Arg Ile Thr Gly Ser Gly Arg Cys Arg Arg Phe Gln Trp Val Asp
                165                 170                 175

Gly Ser Arg Trp Asn Phe Ala Tyr Trp Ala His Gln Pro Trp Ser
                180                 185                 190

Arg Gly Gly His Cys Val Ala Leu Cys Thr Arg Gly Gly Tyr Trp Arg
                195                 200                 205

Arg Ala His Cys Leu Arg Arg Leu Pro Phe Ile Cys Ser Tyr
                210                 215                 220
```

```
(2) INFORMATION FOR SEQ ID NO: 4:

(i) SEQUENCE CHARACTERISTICS:
        (A) LENGTH: 233 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: 220291

(xi) SEQUENCE DESCRIPTION: SEQ ID NO: 4:

Met Lys Leu Leu Leu Leu Ala Leu Leu Gly Ala Val Ser Thr
 1               5                  10                  15

Arg His Leu Lys Val Asp Thr Ser Ser Leu Gln Ser Leu Arg Gly Glu
            20                  25                  30

Glu Ser Leu Ala Gln Asp Gly Glu Thr Ala Glu Gly Ala Thr Arg Glu
            35                  40                  45

Ala Thr Ala Gly Ala Leu Met Pro Leu Pro Glu Glu Glu Met Glu
50                  55                  60

Gly Ala Ser Gly Ser Glu Asp Asp Pro Glu Glu Glu Glu Glu Glu
65                  70                  75                  80

Glu Glu Val Glu Phe Ser Ser Glu Leu Asp Val Ser Pro Glu Asp Ile
                85                  90                  95

Gln Cys Pro Lys Glu Glu Asp Thr Val Lys Phe Phe Ser Arg Pro Gly
            100                 105                 110

Tyr Lys Thr Arg Gly Tyr Val Met Val Gly Ser Ala Arg Thr Phe Asn
            115                 120                 125

Glu Ala Gln Trp Val Cys Gln Arg Cys Tyr Arg Gly Asn Leu Ala Ser
130                 135                 140

Ile His Ser Phe Ala Phe Asn Tyr Gln Val Gln Cys Thr Ser Ala Gly
145                 150                 155                 160

Leu Asn Val Ala Gln Val Trp Ile Gly Gly Gln Leu Arg Gly Lys Gly
            165                 170                 175

Arg Cys Arg Arg Phe Val Trp Val Asp Arg Thr Val Trp Asn Phe Ala
            180                 185                 190

Tyr Trp Ala Arg Gly Gln Pro Trp Gly Arg Gln Arg Gly Arg Cys
            195                 200                 205

Val Thr Leu Cys Ala Arg Gly Gly His Trp Arg Arg Ser His Cys Gly
210                 215                 220

Lys Arg Arg Pro Phe Val Cys Thr Tyr
225                 230

(2) INFORMATION FOR SEQ ID NO: 5:

(i) SEQUENCE CHARACTERISTICS:
        (A) LENGTH: 234 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: 544241
```

(xi) SEQUENCE DESCRIPTION: SEQ ID NO: 5:

```
Met Lys Leu Leu Leu Leu Ala Leu Leu Val Gly Ala Val Ser Thr
1               5                   10                  15

Arg His Leu Asn Val Asp Thr Ser Ser Leu Gln Ser Leu Gln Gly Glu
            20                  25                  30

Glu Ser Leu Ala Gln Asp Gly Glu Thr Ala Glu Gly Ala Thr Arg Glu
            35                  40                  45

Ala Ala Ser Gly Val Leu Met Pro Leu Arg Glu Glu Val Lys Glu Glu
    50                  55                  60

Met Glu Gly Gly Ser Gly Ser Glu Asp Asp Pro Glu Glu Glu Glu Glu
65                      70                  75                  80

Glu Lys Glu Met Glu Ser Ser Ser Glu Leu Asp Met Gly Pro Glu Asp
                85                  90                  95

Val Gln Cys Pro Lys Glu Glu Asp Ile Val Lys Phe Glu Gly Ser Pro
                100                 105                 110

Gly Cys Lys Ile Cys Arg Tyr Val Val Leu Ser Val Pro Lys Thr Phe
            115                 120                 125

Lys Gln Ala Gln Ser Val Cys Gln Arg Cys Phe Arg Gly Asn Leu Ala
    130                 135                 140

Ser Ile His Ser Tyr Asn Ile Asn Leu Gln Val Gln Arg Ser Ser Arg
145                 150                 155                 160

Ile Leu Asn Val Ala Gln Val Trp Ile Gly Gly Gln Leu Arg Gly Lys
                165                 170                 175

Gly His His Lys His Phe His Trp Val Asp Gly Thr Leu Trp Asn Phe
            180                 185                 190

Trp Tyr Trp Ala Ala Gly Gln Pro Trp Arg Gly Asn Asn Ser Gly Arg
        195                 200                 205

Cys Val Thr Leu Cys Ala Arg Gly Gly His Trp Arg Arg Ser His Cys
        210                 215                 220

Gly Val Arg Arg Ala Phe Ser Cys Ser Tyr
225                 230
```